United States Patent [19]
Beer et al.

[11] Patent Number: 4,799,922
[45] Date of Patent: Jan. 24, 1989

[54] BREAST PUMP INSERT

[75] Inventors: Christian Beer, Boniswil; Robert Riedweg, Lucerne; Klaus Schlensog, Hünenberg, all of Switzerland

[73] Assignee: Ameda AG, Zug, Switzerland

[21] Appl. No.: 17,864

[22] Filed: Feb. 24, 1987

[30] Foreign Application Priority Data

Feb. 28, 1986 [CH] Switzerland .................. 00825/86

[51] Int. Cl.$^4$ ............................................. A61M 1/06
[52] U.S. Cl. .................................... 604/74; 604/346; 119/14.49
[58] Field of Search .................... 604/73–76, 604/346; 128/DIG. 21; 119/14.31, 14.47–14.52; D24/14, 23, 24, 47, 51, 55

[56] References Cited

U.S. PATENT DOCUMENTS

| 3,822,703 | 7/1974 | Davisson | 604/75 |
| 4,200,058 | 4/1980 | Happel | 119/14.31 |
| 4,263,912 | 4/1981 | Adams | 604/75 |
| 4,680,028 | 7/1987 | Stuart | 604/316 |

FOREIGN PATENT DOCUMENTS

| 0524638 | 3/1956 | Belgium | 604/346 |
| 0116186 | 8/1984 | European Pat. Off. | 604/74 |
| 2127293 | 4/1984 | United Kingdom | 604/74 |

Primary Examiner—C. Fred Rosenbaum
Assistant Examiner—Mario Costantino
Attorney, Agent, or Firm—Morris Fidelman; Franklin D. Wolffe

[57] ABSTRACT

A breast pump insert formed of a soft, resilient and translucent polymer material, such as a silicon polymer, that is inert against boiling water has a monolithic self-supporting structure consisting of a first or funnel-shaped portion for contact with a nipple-encompassing breast area and for providing a deformable sealing connection between the nipple-encompassing area and the suction bell of the breast pump when the pressure is reduced therein; and of a second or thimble-shaped portion for maintaining an enclosure around the nipple-encompassing area when the pressure is reduced within the pump; the thimble-shaped portion of the insert has an elongated and essentially tubular longitudinal wall section and an essentially transverse end wall section that provides a helmet-shaped end of the structure and includes at least one perforation for permitting passage of milk; the timble-shaped portion is formed and dimensioned to prevent axial collapse thereof under normal use conditions.

6 Claims, 4 Drawing Sheets

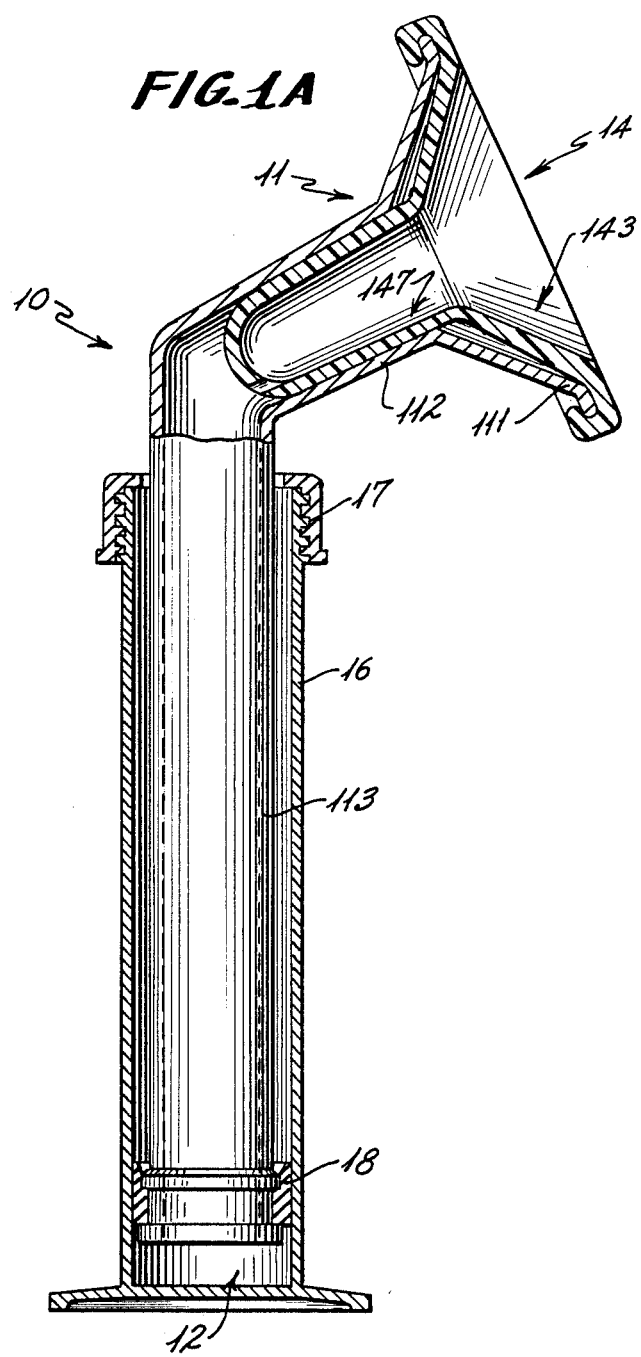

BREAST PUMP INSERT

BACKGROUND OF THE INVENTION (a) Field of the invention

This invention generally relates to breast pumps and to improvements in breast pump operation with regard to interaction between pump and the breast of a mother. More specifically, the invention relates to a novel insert for conventional breast pumps of the type comprising a suction means which may be operated manually or mechanically, e.g. electrically, and having a milk reservoir which may but need not serve as the milk recipient portion of a baby feeding-bottle.

(b) Description of the prior art

Manually and mechanically operated breast pumps of the above mentioned type have been disclosed, for example, in our U.S. Pat. No. 4,573,969 as well as in our U.S. Application Ser. No. 06/711,676 and our GB - A - No. 8506679, and may include an insert for improved adaption of the suction bell made of a generally rigid material, such as glass or an organic polycarbonate, to a mother's breast.

Further, U.S. Pat. No. 3,977,405 teaches use of an annular insert made of an elastomer, e.g. rubber, for stabilizing the nipple or, actually, the nipple position within the suction bell made of a generally rigid organic polymer.

Another type of a soft insert in a breast pump having a rigid suction bell is disclosed in U.S. Pat. No. 3,822,703 and is a circular diaphragm in sealing connection with the suction bell; the diaphragm is provided with a central aperture dimensioned such that but the nipple area of the breast may extend therethrough; another breast pump with a diaphragm-type contact face for the nipple-encompassing area is disclosed in U.S. Pat. No. 2,542,505 but in either case the membrane has a substantially uniform thickness and is opaque.

Other types of breast pumps, i.e. those comprising a suction bell of an opaque and relatively non-rigid material, such as rubber, have been disclosed in U.S. Pat. No. 4,323,067 as well as in French Pat. No. 1,067,421 and include a deformable portion for contact with the nipple-encompassing area of a mother's breast which portion may be integrally connected with the suction bell or may be formed as an insert for same but in either case is subject to an above-ambient pressure applied from the backside of the deformable portion.

Finally, breast-contact pieces made of an opaque and deformable material for connection with a pump or pump recipient and entirely without support by an external suction bell or "flange" have been disclosed in French Pat. No. 1,091,809.

Obviously, a pump that includes a deformable contact portion in the nipple-encompassing area could be capable of simulating the "suckling" effect of palate and mouth of a baby and the advantages of such "simulating" pumps have been postulated for more than 30 years.

Yet, market researches made before the present invention seem to indicate a general user preference for breast pumps of the type having a suction bell formed of a rigid and heat resistant glass-like material because of their simple structure combined with transparence or translucence of the main pump components so as to enable safe and easily controllable cleaning in the same way as baby feeding bottles are cleaned, i.e. by immersing milk-exposed breast pump components in boiling water and visual control of the results.

OBJECTS AND SUMMARY OF THE INVENTION

Accordingly, it is a main object of the invention to provide for an easily mountable and dismountable breast pump insert of simple construction that can be used with, and similarly cleaned and controlled as, breast pumps of the generally transparent type having an essentially rigid suction bell while, at the same time, providing for a deformable contact face member capable to cause lateral nipple-compression and aureola contact similar to that of a suckling infant.

Another important object is to provide for an insert for a prior art breast pump so as to generally improve pump effectiveness by post-fitting such pump with the insert.

Yet a further object is to provide for a novel breast pump combining the best features of transparent or translucent devices that can be sterilized in boiling water with the advantages of a deformable and easy-to-use contact member that simulates the impact of a suckling infant upon the mother's nipple and aureola while requiring neither a sophisticated pump structure nor support devices for generating above-ambient pressure.

Further objects and advantages of the invention will become apparent as this specification proceeds.

Briefly, according to a first general embodiment the present invention provides for an insert for a breast pump of the type comprising a milk reservoir, an essentially rigid and generally transparent or translucent suction bell having a flared open end, and a suction means for temporarily reducing an ambient pressure within the pump; said insert being formed of a soft, resilient, and preferably translucent polymer material that is inert against water at a temperature of at least about 100° C.; the insert is a substantially monolithic self-supporting structure consisting of (i) a funnel-shaped first portion for sealing contact with a nipple-encompassing area of a mother's breast when the ambient pressure is reduced within the pump for milk extraction; and (ii) an elongated thimble-shaped second portion capable of defining an enclosure around the nipple-encompassing area when the ambient pressure is reduced; the funnel-shaped first portion of the insert structure includes an annular deformation zone which has a predetermined wall thickness; the elongated thimble-shaped second portion of the insert structure comprises an essentially tubular longitudinal wall section and an essentially transverse end wall section which preferably provides a helmet-shaped end of the insert and has at least one perforation for permitting milk to pass to the reservoir; the thimble-shaped second portion of the insert is formed and dimensioned to prevent axial collapse thereof under normal use, i.e. inserting into the pump and pump operation, and has a wall thickness that is greater than the reduced wall thickness of the deformation zone.

BRIEF DESCRIPTION OF THE PREFERRED EMBODIMENTS

The generally preferred way of providing the insert with a monolithic and self-supporting structure is to provide it in the form of a molded integral (i.e. one-piece) structure made of a soft, resilient, translucent and heat sterilizable (i.e. resistant against boiling water at ambient or reasonably elevated pressures encountered in autoclaves and pressure cookers for home use) polymer, such as commercial silicone rubber as accepted for medical use under FDA 177.260 and BGA XXI Standards. Specific examples will be given below.

The insert is self-supporting in the sense that it is capable to maintain its normal operative shape without external support; while the overall resilience of the insert is that of the constituting polymer the inventive insert will be substantially less deformable in its thimble-shaped second portion ("thimble" for short) than in the annular deformation zone of its funnel-shaped portion ("funnel" for short). As already indicated, the wall thickness ratio is an essential first parameter; the second essential parameter resides in the relative shape effects of the thimble, on the one hand, and the funnel, on the other. Thus, the thimble is "elongated" in the sense that it has an internal width: length ratio of below 1, e.g. about 0.5, so that the length of the enclosure formed by the thimble of the insert and extending from the nipple-encompassing area in the direction of the nipple axis is greater than the maximum internal width of that enclosure, e.g. greater by a factor of from 1.5 to 3.

Further, the transverse end wall section of the thimble is essential for an integral self-supporting insert: it must provide sufficient stability of shape such that the thimble will be essentially non-collapsible under normal use conditions; for example, a typical use load, e.g. the force used to push the insert into the suction bell of a breast pump for mounting, or the pressure differential between ambient pressure acting upon an inner surface portion of the insert and the reduced pressure or suction within the pump acting upon an outer surface portion of the insert, should cause no significant deformation of the thimble in longitudinal (i.e. axial) direction and, preferably, such loads should cause no substantial deformation of the thimble in transverse (i.e. radial) direction either.

A generally preferred means to achieve optimal shape stability of the thimble, aside from the above mentioned wall thickness ratio, is to shape the transverse end wall section of the thimble in the manner of a helmet; this will generally include a more or less curved, e.g. "domed" or "calotte-shaped" outer surface of the end wall; the inner surface (nearer to the mother's breast) of the thimble end wall may also be curved but could have a larger diameter of curvature such that the end wall section of the thimble will be thicker than the longitudinal wall section, e.g. by a factor of typically about 1.5 to 4.5, e.g. about 3.

In connection with the shape stability contribution of the transverse end wall it should be mentioned that milk passage openings are provided in that wall, and that the shape, size, and distribution of such passages may influence shape stability and should be considered when selecting a particular shape and thickness of the helm-shaped end. Typically, the openings will cover but a minor part of the total end wall area, e.g. less than 50% thereof, and preferably not more than 30%, to prevent undue reduction of the shape stability contribution of the end wall.

It should be noted that shape stability of the thimble has a critical aspect insofar as any deformation thereof caused by any pressure difference between ambient pressure and the reduced pressure which the pump may generate is restricted essentially to some, if any, deformation in radial direction; in other words, any such pressure-induced deformation of the elongated thimble must not cause contact with the "front surface" of the nipple, i.e. the nipple portion where the passages from the milk glands end. Thus, contact, if any, between the thimble and a mother's nipple must be limited to "lateral" portions of the nipple. By the same token, the internal diameter of the thimble should be large enough to accomodate large diameter nipples.

While the shape of the longitudinal wall section of the thimble is "essentially tubular" in the sense that it has an essentially circular cross-section in a radial plane, the diameters of such cross-sections at different points along the longitudinal axis of that portion need not be the same. In fact, a more or less conical shape (enclosed angle typically between about 0° and about 30°, e.g. between about 5° and 20°) of the thimble may be preferable for many purposes since preferred pumps for use with the insert according to the invention have a conical section next to their flared open end portion. Normally, the maximum internal diameter of the thimble is at the end thereof adjacent the funnel.

Preferably, one or more protrusions, e.g. in the form of lip seal members, are provided at the outer side of the longitudinal wall section of the thimble for sealing connection with an essentially tubular (i.e. including conical with an aperture angle of, say, up to 30°) portion of the rigid suction bell of the pump. Preferably, at least one of these protrusions serves as a stop means to limit movement of the insert into the corresponding rigid suction bell portion that receives and holds the thimble during pump operation.

The funnel of the insert includes the annular deformation zone which, typically, extends essentially from the junction of thimble and funnel to a peripheral edge section thereof for slip-on connection of the insert with the open end of the rigid suction bell so as to provide for easy assembly and disassembly of insert and pump.

Preferably, the edge section of the funnel has an increased wall thickness relative to the adjacent deformation zone and includes an air channel means for reasons explained below.

BRIEF DESCRIPTION OF THE DRAWINGS

The invention will be better understood and objects other than those set forth above will become apparent when considering the following detailed description thereof. Such description makes reference to the annexed drawings which illustrate preferred exemplary embodiments of the invention and wherein:

FIG. 1A is a partially sectional side view of a prior art breast pump provided with an insert according to a first embodiment of the invention shown in a diagrammatic crosssectional view.

DETAILED DESCRIPTION OF THE PREFERRED EMBODIMENTS

Figure 1B:
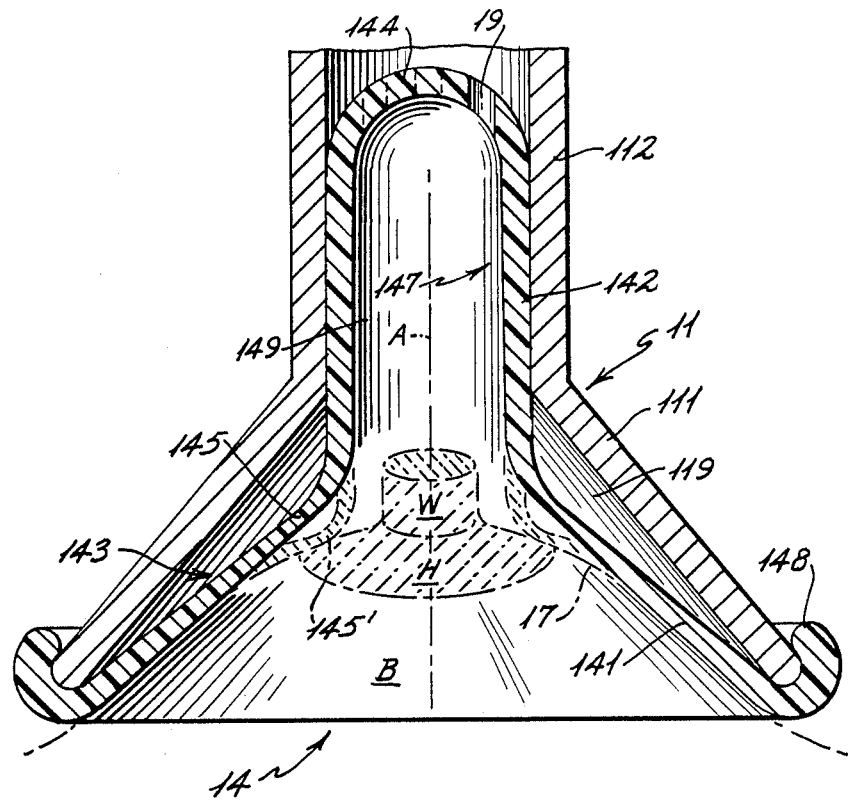
FIG. 1B is an enlarged diagrammatic view of the suction bell portion of the pump of FIG. 1A.
Figure 1C:
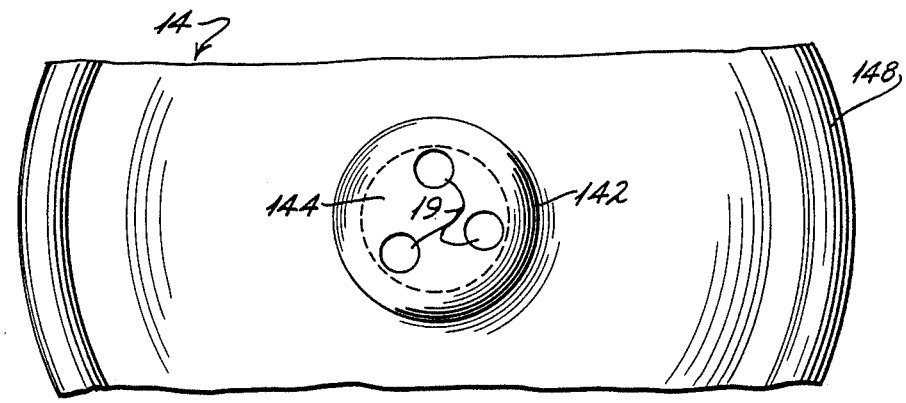
FIG. 1C is a top plan view of FIG. 1B for illustrating the milk passage of an inventive insert.
Figure 2:
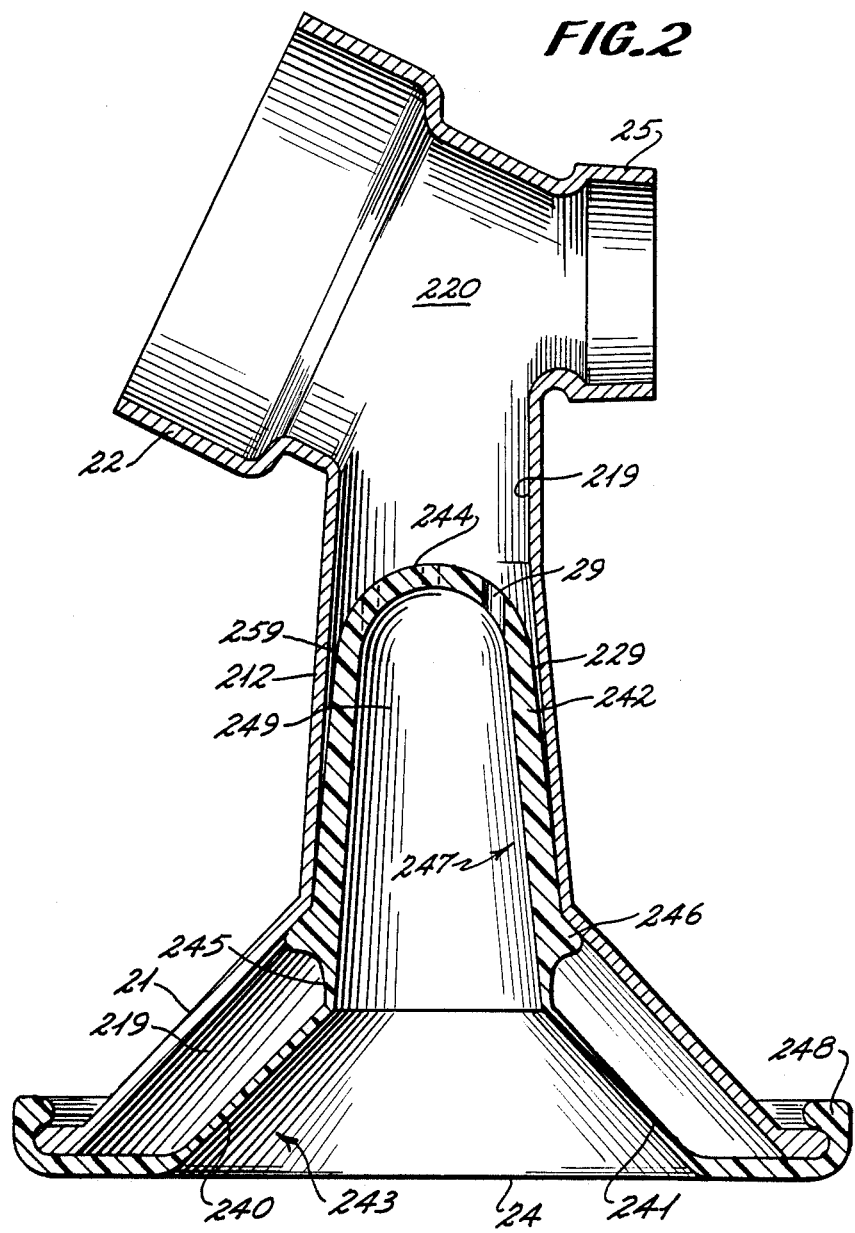
FIG. 2 is a sectional side view of another type of breast pump with a diagrammatic illustration of an insert according to the invention.

Specifically, the breast pump 10 of FIG. 1A is that illustrated in FIGS. 1-3 of our commonly assigned U.S.

Pat. No. 4,573,969 except that the rigid insert 14 shown in the said Patent is replaced by an insert according to the present invention.

However, use of the non-rigid insert disclosed herein is not restricted to such pumps. Other suitable pumps for postfitting with the inventive insert are those disclosed in the above mentioned U.S. Application Ser. No. 06/711,676, the British Specification GB - A - No. 8506679 as well as the breast pumps rented or sold under the EGNELL (registered trademark) label, and all of which have a rigid suction bell portion with shapes and dimensions substantially as shown for suction bell 11 in FIG. 1.

In fact, geometry and dimensions of suction bell 11 of U.S. Pat. No. 4,573,969 as reproduced herein in FIG. 1 have been accepted by various breast pump manufacturers to the point of establishing an industrial standard such that an insert according to the present invention shaped to match the dimensions of suction bell 11 herein will be suitable for a substantial part of the commercially available breast pumps sold under various brands and labels.

Accordingly, the disclosure of U.S. Pat. No. 4,573,969 is incorporated by way of reference into the present specification for explaining structure and function of a representative prior art breast pump which can be improved, as regards effectiveness and user comfort, by a soft insert according to the present invention.

Briefly, this species of a manually operated breast pump 10 is provided with a rigid suction bell portion 11 having a flared open ended portion 111 and a tubular and slightly conical connection 112 which is integrally connected with the inner tube 113 of a piston/cylinder-type suction pump arrangement formed with an outer cylinder 16 that also serves as a milk reservoir. A one-way sealing ring 18 is provided at the lower end of tube 113, and a screw-cap 17 serves to prevent unintentional withdrawal of tube 113 from cylinder 16 upon upward movement for increasing the inner volume or space 12. When the inner volume or space 12 is increased by relative outward movement of tube 113, and while suction bell 11 is closed by a mother's breast (cf. FIG. 1B), the ambient pressure in space 12 will be temporarily reduced and controlled by the user's handling of the pump and the effectiveness of the sealing connections formed by ring 18 within the pump and by the breast B shown diagrammatically in FIG. 1B.

With a conventional pump 10 breast B would be in contact with the inner surface of suction bell portion 111 made of a transparent but rigid material, such as glass or a polymer that is substantially inert against boiling water, or a prior art rigid-type insert.

According to the present invention insert 14 is made of a soft and resilient polymer, such as an elastomer of the silicone rubber type obtainable, e.g. from reactive organo siloxane compounds, polymerized and cured to provide a physiologically safe translucent or transparent rubber-type material that can be sterilized in hot air, water or steam at temperatures of typically from 95° to 120° C.

Preferred silicone elastomers for use in the present invention have a shore-A hardness of from about 35 to about 55, a tensile strength of from about 6 to about 12 Newton per square millimeters, an elongation at break of from about 500 to about 800 percent and a residual stress rating under constant deflection of not more than about 35% when tested after 22 hours at 175° C., all values measured by standard testing methods as specified, for example, in German Standards DIN 53504 (March 1985) and DIN 53517 (January 1972).

According to the present invention breast B is in contact with an insert 14 made of such a soft and resilient elastomer; insert 14 is an integral monolithic structure consisting of a funnel-shaped portion or, briefly, "funnel" 143 and a thimble-shaped portion or, briefly, "thimble" 147.

Funnel 143 is formed by a wall 141 extending from edge portion 148 through a deformation zone 145 of reduced wall thickness to the lower end portion 140 of thimble 147. Edge portion 148 engages with the open end of the flared suction bell portion 111 while the longitudinal wall section 142 of thimble 147 engages with tubular suction bell portion 112.

An annular chamber 119 is formed between insert 14 and suction bell 11, and an air passage means (not shown in FIG. 1) is provided for connection of chamber 119 with the ambient atmosphere.

Wall 142 of thimble 147, on the other hand, is sealingly connected with suction bell portion 112 so that a temporary reduction of pressure within pump 10 (FIG. 1A) will also reduce the pressure within enclosure 149 due to milk passages 19 provided in the helmet-shaped transverse end wall section 144 of thimble 147 if wall section 141 of funnel 143 forms a sealing connection 17 with breast B.

Since chamber 119 remains at ambient pressure, a pressure reduction within enclosure 149 will cause that wall section 145 of funnel 143 is pressed onto breast B in the aureola region H that encompasses nipple W.

In breast pumping operation the longitudinal axis A of the tubular wall section 142 of thimble 147 should be in substantial alignment with the "breast axis" defined by a line that extends through the center of nipple W and is essentially parallel to the longitudinal extension of nipple W, i.e. essentially parallel to the sides of nipple W.

Due to the shape stability of thimble 147 and the predetermined reduced wall thickness of deformation zone 145, normal pressure reductions within pump 10 and within enclosure 149 will substantially prevent collapsing of thimble 147 in axial (A) direction, and any deformation of enclosure 149 will be in radial direction. Thus, any contact between nipple W and any wall section of insert 14 will be limited to the sides of nipple W while no contact with the sensitive front face thereof is possible. The shape stability of thimble 147 is also important for easy mounting of insert 14 within suction bell 11 and dismounting, e.g. for cleaning and sterilization of all breast- and milk-contacting parts of pump 10.

It will be understood that axis A would not actually be in the position shown in FIG. 1B when the pump is in contact with breast B; the normal position of the torso of a mother using pump 10 would be vertical or inclined backwards so that axis A would be in a correspondingly inclined position. Accordingly, milk emerging from nipple W will flow in a downward stream along wall 142 and through opening 19 into the milk reservoir within cylinder 16 (FIG. 1A).

As shown in FIG. 1C, an array of several openings 19 will be provided in end wall 144 so that passage of milk without substantial accumulation within enclosure 149 will be ascertained regardless of the radial position of insert 14 relative to suction bell 11. Obviously, an array of three or more openings is suitable keeping in mind that the shape stability of thimble 147 must not be unduly reduced.

FIG. 2 is a somewhat enlarged diagrammatical view of a modification of an insert 24 according to the invention when mounted in the rigid suction bell of another prior art breast pump of the type disclosed in U.S. Ser. No. 711,676 or GB - A - No. 8506679 for operation with a battery-driven electric motor.

Such a suction bell comprises a first flange 22 (internal thread not shown) for connection with a milk reservoir (not shown) and a second flange 25 for connection with a pump/motor/battery unit (not shown) so as to reduce ambient pressure within space 220 and to also reduce ambient pressure within enclosure 249 when the latter is closed by a breast (not shown) in sealing contact with surface 240 of wall section 241 of an inventive insert structure 24 formed by a funnel 243 and a thimble 247, both made of a soft and resilient elastomer of the type defined above.

The outer end portion of funnel 243 is shaped to provide a slip-on connection 248 with the open end of suction bell portion 21 and thimble 247 engages with the suction bell by means of an external protrusion 246 in the area of the junction between the tubular (conical) portion 212 of the rigid suction bell and its flared portion 21.

Again, an air passage means (not shown) is provided so that the annular space 219 formed between the rigid suction bell wall 21 and the relatively thin wall 241 of the annular deformation zone of funnel 243 remains at ambient pressure when the pressure within space 220 is reduced while funnel 243 is sealed by a breast along surface 240, and the nipple-encompassing enclosure 249 is under reduced pressure because of milk passage ducts 29 in the helmet-shaped transverse wall section 244 of thimble 247.

The outer surface 249 of thimble 247 may be provided with annular protrusions (not shown) so as to seal gap 229 between wall 212 of the suction bell and the longitudinal wall section 242 of thimble 247. As is diagrammatically indicated in FIG. 2, the gap 229 may be a convergent gap formed between conical outer surface 259 of thimble 247 and the conical inner surface 212 of the suction bell. Obviously, such difference of conical surfaces may facilitate fitting of differing pumps with standardized inserts.

External protrusion 246 of thimble 247 will not only provide a seal between spaces 219 and 220 for deformation of wall 240 in accordance with a pressure difference in such spaces but also permit movement of the thimble portion 247 of the inventive insert into the suction bell portion 212. A defined junction line 245 may be provided between thimble 247 and funnel 243 and could be determined by the annulus where the greater thickness of the longitudinal thimble wall section 242 reaches the predetermined reduced thickness of the annular deformation zone 241 but this is not believed to be critical.

Figure 3A:
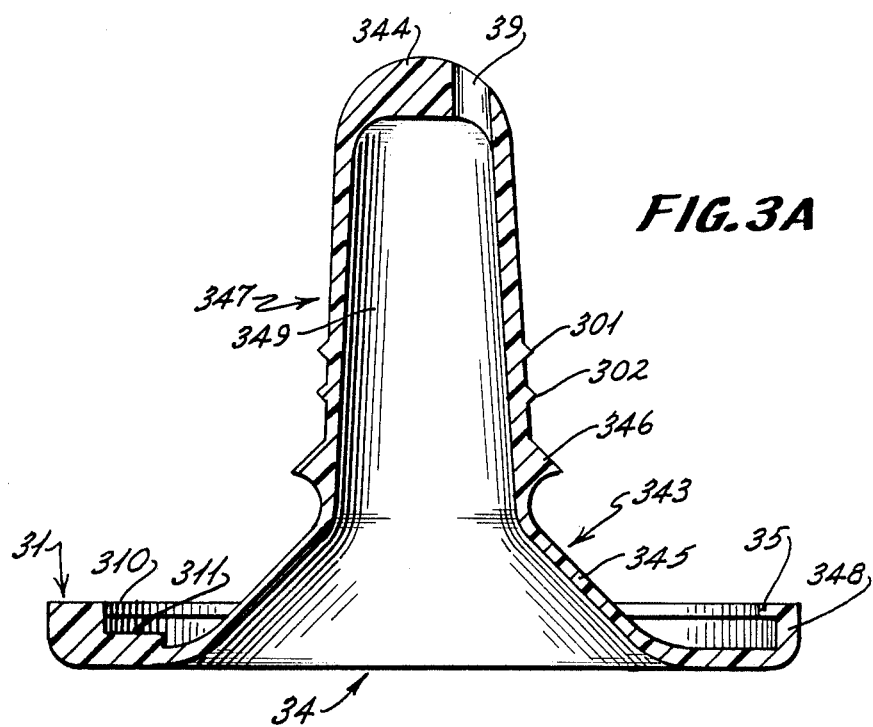
FIG. 3A is a sectional and somewhat enlarged view of a preferred embodiment of the insert according to the invention.
Figure 3B:
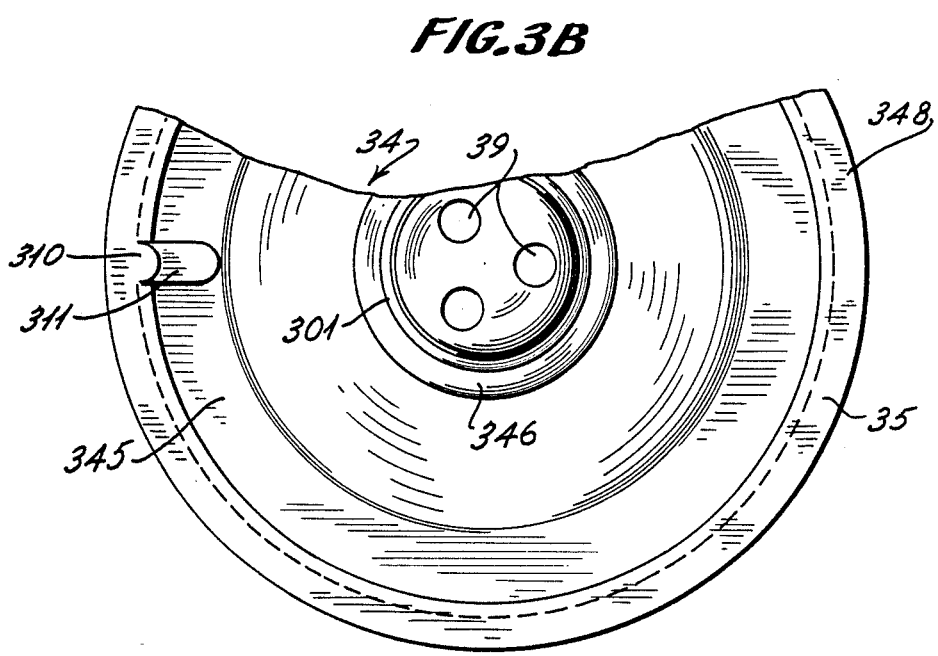
FIG. 3B is a top plan view of the insert shown in FIG. 3A.

FIGS. 3A and 3B show a preferred embodiment of an insert 34 according to the invention in a slightly enlarged cross-sectional view (3A) and plan top view (3B).

Insert 34, again, is an integral monolithic structure made of a soft, resilient and translucent elastomer of the type defined above and consisting of a funnel 343 and a thimble 347. As apparent from FIG. 3A, the annular deformation zone 345 has a thickness that is smaller than that of thimble 347 but the shape stability thereof, notably against collapsing, i.e. compressive deformation in axial direction, is achieved with a relatively thin longitudinal wall section 342 and a helmet-shaped transverse end wall section 344 that is about three times thicker than section 342 which, in turn, is about twice as thick as the annular deformation zone 345. Due to the enlarged thickness of end wall 344, milk passage perforations 39 will have no negative impact upon shape stability of thimble 347 and the nipple-encompassing enclosure 349 formed by end wall 344 and longitudinal wall 342 will not collapse in axial direction under normal use conditions.

Annular lip-seal members 301, 302 are provided for sealing engagement with the inner surface of a tubular (including conical) suction bell portion (not shown) while a larger protrusion 346 serves both as a sealing means and as a stopper to limit motion of insert 34 into the suction bell of a standard breast pump.

The wall thickness of the annular deformation zone 345 of funnel 343 increases from a predetermined reduced thickness both toward thimble 347 as well as toward the peripheral end portion 348.

In order to ascertain that the annular space (not shown) formed between the outer surface of funnel 343 and the inner surface of the rigid suction bell of the pump (not shown) will be at ambient pressure even when enclosure 349 is at reduced pressure, an air passage means 31 is formed by a pair of surface protrusions 310, 311 formed at a segment of the peripheral end portion 348 which has a rim 35 for slip-on connection with the circular peripheral end (not shown) of a standard rigid suction bell so as to preclude that a sealing connection is formed by edge 35, 348 of insert 34 with the rim or edge of the rigid suction bell of the pump.

It is to be noted that insert 34 is shown in a somewhat enlarged form. For many commercial pumps an insert diameter of about 80 mm (as defined by the broken circular line of FIG. 3B) is typical.

User tests made with pump inserts according to the present invention in combination with commercially available breast pumps of all kinds mentioned herein have shown full if not enthusiastic acceptance; for example, when using the insert of FIG. 3 with a pump according to GB - A - No. 8506679 and slowly turning the suction bell plus insert for a circular massage effect upon the aureola, pumping-off was generally achieved in a more complete manner (10–20% increases of yield) and within substantially shorter periods of typically about 10 to 12 minutes as opposed to 20 to 25 minutes with the same pump but without the insert. Generally, prolactin production was improved by prolonged use of the pump plus insert as evidenced by improved breast productivity.

Regardless of the type of pump used with the insert, i.e. with manually operated, hand-held battery-operated pumps and rent pumps (e.g. EGNELL, registered trademark), the invention, as confirmed by user tests, provides the following advantages:

all areas of the breast can be emptied;

increased flow and volume of milk while stimulating the so-called "let-down" reflex as well as prolactin production;

choice between various commercial pumps is possible without sacrificing comfort;

aureola as well as nipple are encompassed and compressed just as if a baby feeds, i.e. substantially complete simulation of suckling action is achieved;

transparent insert permits visual control of nipple position and milk flow;

simultaneous gentle massage can be achieved while pumping;

simplicity of use and cleaning, e.g. by sterilization in boiling water, in dishwasher, or in autoclave.

While there are shown and described present preferred embodiments of the invention, it is to be distinctly understood that the invention is not limited thereto but may be embodied and practiced within the scope of the following claims.

Accordingly, what we claim is:

1. In a breast pump of the type comprising a milk reservoir, an essentially rigid suction bell having a flared open end, and a suction means for temporarily reducing an ambient pressure within said pump, the improvement consisting essentially of an insert:

having a funnel shape with a conical mouth portion for sealing contact with a nipple encompassing area of a mother's breast when ambient pressure is reduced within said pump and an apex section for directing milk into the milk reservoir;

said conical mouth portion comprising a deformable conical wall portion capable of deflecting for pressing against the mother's breast in the encompassed area around the encompassed nipple when ambient pressure is reduced within said pump;

said apex section being thimble shaped with an essentially tubular side wall and an apertured end face wall, both of which are non-deformable when ambient pressure is reduced within said pump;

said funnel shape insert thereby defining an enclosure around said nipple-encompassing areas when ambient pressure is reduced within said pump, said enclosure being subjected to the pressure changes whereby mother's milk becomes drawn from the nipple into said insert and flows out therefrom through said apertured end face wall; and means on said funnel shape insert for positioning said insert sealed and secured in said suction bell such that the outside surface of said conical wall portion thereof but not of said thimble portion thereof faces the non-varying ambient pressure outside of said suction bell, whereby operation of said suction means reduces ambient pressure inside said insert causing only said deformable conical wall portion thereof to deflect as aforesaid.

2. The insert of claim 1 wherein said thimble-shaped portion has at least one external protrusion for sealing connection with a conical portion of said rigid suction bell.

3. The insert of claim 1 wherein at least one of said protrusions is capable to act as a stop means for limiting movement of said thimble-shaped portion of said insert into said conical portion.

4. The insert of claim 2 wherein at least one of said external protrusions is formed as a lip seal member.

5. The insert of claim 1 wherein said funnel-shaped portion of said insert has a peripheral edge section for slip-on connection with said open end of said suction bell; said edge section including an air channel means to permit that ambient pressure is maintained at a backside portion of said deformation zone.

6. The breast pump of claim 1 wherein an annular chamber is provided between said rigid suction bell and said funnel-shaped portion of said insert structure, and wherein an air channel means is provided for maintaining in said annular chamber a pressure that is higher than the pressure within said pump when said ambient pressure is reduced therein.

* * * * *